United States Patent [19]

Goldberg et al.

[11] Patent Number: 5,474,075
[45] Date of Patent: Dec. 12, 1995

[54] BRUSH-TIPPED CATHETER FOR ULTRASOUND IMAGING

[75] Inventors: Barry B. Goldberg, Oreland, Pa.; Ji-Bin Liu, Voorhees, N.J.; Robert M. Steiner, Wynnewood, Pa.

[73] Assignee: Thomas Jefferson University, Philadelphia, Pa.

[21] Appl. No.: 157,640

[22] Filed: Nov. 24, 1993

[51] Int. Cl.⁶ ............................ A61B 8/12
[52] U.S. Cl. ............... 128/622.06; 128/756
[58] Field of Search ............ 128/600.03, 662.06, 128/662.03, 756

[56] References Cited

U.S. PATENT DOCUMENTS

| | | | |
|---|---|---|---|
| 4,671,295 | 6/1987 | Abrams et al. | 128/662.06 |
| 4,722,347 | 2/1988 | Abrams et al. | 128/662.06 X |
| 4,742,829 | 5/1988 | Law et al. | 128/622.05 |
| 4,763,670 | 8/1988 | Manzo | 128/756 |
| 4,850,957 | 7/1989 | Summers | 604/22 |
| 4,886,059 | 12/1989 | Weber | 128/662.06 X |
| 4,946,440 | 8/1990 | Hall | 604/95 |
| 4,951,677 | 8/1990 | Crowley et al. | 128/662.06 |
| 5,090,414 | 2/1992 | Takano | 128/662.06 X |
| 5,190,045 | 3/1993 | Frazin | 128/662.06 |
| 5,201,323 | 4/1993 | Vermeulen | 118/756 |
| 5,203,338 | 4/1993 | Jong | 128/662.06 |
| 5,325,860 | 7/1994 | Seward et al. | 128/662.06 |
| 5,331,947 | 7/1994 | Shturman | 128/662.06 X |
| 5,345,940 | 9/1994 | Seward et al. | 128/662.06 |

OTHER PUBLICATIONS

Ikeda, S., "Flexible broncho–fiberoscopy," *Ann Otol Rhinol Laryngol*, 79, 916–923 (1970).

Shure, D., "Fiberoptic Bronchoscopy: diagnostic applications," *Clin Chest Med*, 8, 1–13 (1987).

Saito, T., et al., "Ultrasonographic approach to diagnosis of chest wall tumors," *Chest*, 94, 1271–1273 (1988).

Izumi, S., et al., "Ultrasonically–guided aspiration needle biopsy in diseases of the chest," *Am Rev Respir Dis*, 125, 460–464 (1982).

Goldberg, B. B., et al., "Sonographically guided laparoscopy and mediastinoscopy using miniature catheter based transducers," *J Ultrasound Med* 12, 49–54 (1993).

Liu, J. B., et al., "Transnasal US of the esophagus: preliminary morphologic and function studies," *Radiology*, 184, 721–727 (1992).

B. Goldberg, et al., "Endoluminal US: Experiments with Non–vascular Uses in Animals," *Radiology*, 174:39–43.

*Primary Examiner*—Francis Jaworski
*Attorney, Agent, or Firm*—Woodcock Washburn Kurtz Mackiewicz & Norris

[57] ABSTRACT

Miniature catheter-based ultrasound transducers are used to image peritracheal or bronchial structures including masses, lymph nodes, and vessels. Most preferably, a 6.2 French catheter containing either a 12.5 or 20 MHz ultrasound transducer coupled with an ultrasound unit is passed through the working channel of a flexible bronchoscope and directed to the region of interest. Patients with pulmonary masses detected by X-ray or computed tomography were studied and it was found that characteristic ultrasound patterns of masses, lymph nodes and blood vessels could be distinguished. Thus, catheter-based ultrasound transducers are useful to evaluate a variety of bronchopulmonary abnormalities. This approach was found to be valuable in the selection of the appropriate site for biopsy. In accordance with the present invention, an improved ultrasound catheter that incorporates a biopsy brush is therefore disclosed.

12 Claims, 1 Drawing Sheet

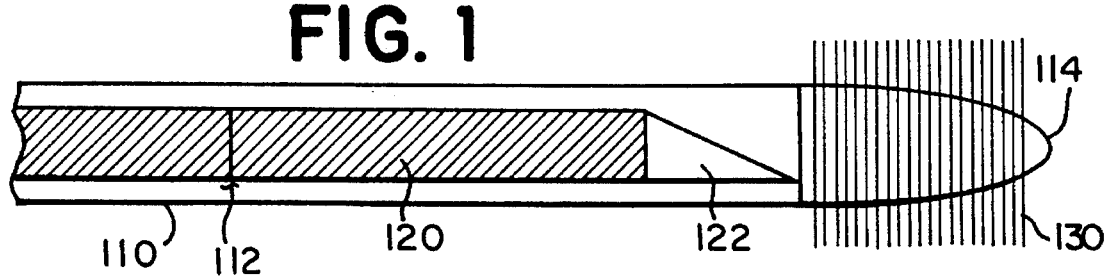
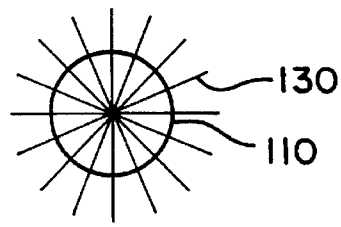
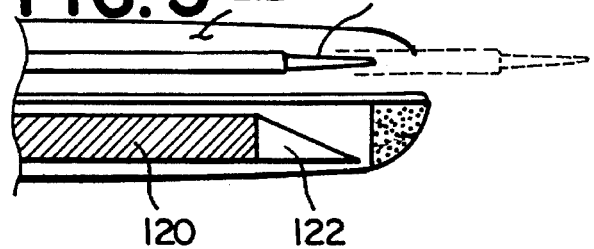
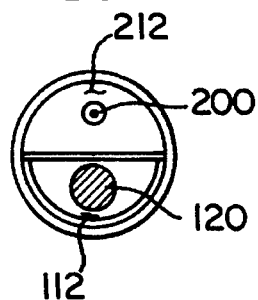

BRUSH-TIPPED CATHETER FOR ULTRASOUND IMAGING

The present invention relates to methods and apparatus for ultrasonic imaging to determine the location of a lesion or other mass and, more particularly, to retrieve a sample of this tissue, i.e., perform a biopsy.

BACKGROUND OF THE INVENTION

The examination of respiratory tract tissue via fiberoptic bronchoscopy is a well-established technology, and its limitations are also known. For example, if a lesion is peripheral it may not be clear, even with fluoroscopy, whether a biopsy is obtained from the abnormality itself or from nearby non-representative tissue. Because the bronchoscope cannot reach beyond the fourth order bronchi, the diagnostic yield of peripheral masses by current methods of bronchoscopic biopsy is significantly lower than obtained in central lesions.

Fiberoptic brochoscopy was introduced in the late 1960s to allow direct visualization of the tracheobronchial tree. Ikeda, S., "Flexible broncho-fiberoscopy," *Ann Otol Rhinol Laryngol*, 79, 916–923 (1970); Shure, D., "Fiberoptic Bronchoscopy: diagnostic applications," *Clin Chest Med*, 8, 1–13 (1987). With this modality, it is possible to detect abnormalities of the tracheobronchial tree, including intraand extraluminal masses, acute and chronic inflammation, and lymphadenopathy. Bronchoscopic signs of disease, including mural deformity and fixation as well as endoluminal obstruction, are used to determine the site for biopsy in order to obtain tissue either directly from the area of suspected primary disease or from involved lymph nodes.

Aided by standard chest radiography, computed tomography, and fluoroscopy during bronchoscopy, it is currently possible to further localize extraluminal tumor or lymph nodes that are amenable to transbronchial biopsy, but, in spite of radiographic guidance and visible deformity, the precise location of extraluminal masses or lymph nodes viewed through the bronchoscope may not be apparent. It is also usually not possible to identify major pulmonary and mediastinal blood vessels, let alone separate arterial from venous structures. If a tumor is necrotic, the preferred site for biopsy may be at the periphery of the lesion and not identifiable with either fluoroscopy or fiberoptic bronchoscopy. If the lesion is peripheral, it may not be clear even with fluoroscopy whether a biopsy specimen is obtained from the abnormality itself or from nearby nonrepresentative tissue.

Since its introduction, fiberoptic bronchoscopy has evolved into one for the most common procedures for the diagnosis of pulmonary disease. Improvements in bronchoscopic optics and imaging acquisition technology as well as in the tissue sampling capabilities of the procedure have expanded its applications, resulting in an overall positive yield of over 90% in cases of obstructing carcinoma. At the same time, as noted above, the limitations of transbronchoscopic biopsy are well recognized. It is often difficult to achieve positive results in cases of necrotic tumors or small peripheral submucosal or peribronchial neoplasms. Tracheal lesions are often difficult to sample accurately because of the angle of the biopsy needle in relation to the tracheal wall. The diagnostic yield of peripheral masses at bronchoscopy is considerably lower than that of central endobronchial lesions, with reported yields of transbronchial biopsy and brushing in the range of 30%– 60%. Small peripheral lesions 3 cm or less in diameter are particularly difficult to characterize with fiberoptic transbronchial biopsy, in part because only one or two bronchi traverse lesions of this size. However, three or more bronchi may be encompassed by larger lesions, increasing the chance that the bronchoscopic forceps or needle will locate the correct site for biopsy.

Supplementary imaging techniques have been helpful in increasing the yield of fiberoptic bronchoscopy in both central and peripheral lesions. Biplane or C-arm fluoroscopy has been particularly useful in increasing the diagnostic yield of the bronchoscopic procedure by demonstrating the location of the forceps or needle in the region of the mass. Pre-procedural planning with high resolution or conventional computed tomography also aids in establishing an appropriate bronchoscopic approach.

In peripheral lesions, fluoroscopy clearly shows the relationship of the tip of the bronchoscope to the mass in the anterior-posterior projection. However, the intubated bronchus may actually lie in front of or behind the mass, and, as a result, the biopsy may not yield positive results. Although computed tomography with 5-mm sections through the mediastinum clearly demonstrates the bronchial anatomy in relation to the suspected mass, it is difficult to precisely duplicate the relationship of the mass, nodes, and vessels—particularly in the case of extraluminal masses.

Thus, it would be desirable to be able to more specifically locate a lesion or other site under study. It would also be desirable to provide methods and apparatus such that upon location, a biopsy could be performed at the site. Therefore, it is an object of the present invention to provide improved methods and apparatus for visualizing the tissue within a patient, and in particular tissue in the tracheobronchial tree. It is another object of the present invention to provide improved methods and apparatus for taking a biopsy.

Thoracic ultrasound has been used for the study of masses and other abnormalities of the chest wall, pleura, lung parenchyma, and mediastinum, the incompatible size of conventional ultrasound transducers compared with the diameter of the biopsy channel of the standard adult-size bronchoscope precluded its use in the past. Saito, T., et al., "Ultrasonographic approach to diagnosis of chest wall tumors," *Chest*, 94, 1271–1273 (1988); Izumi, S., et al., "Ultrasonically-guided aspiration needle biopsy in diseases of the chest," *Am Rev Respir Dis*, 125, 460–464 (1982).

Miniature catheter-based ultrasound transducers with a diameter of 3.5 to 6.2 French have been used in conjunction with flexible endoscopy of the genitourinary and gastrointestinal tracts because of their ability to image beyond the luminal surface, providing information about the exact location of masses as well as such normal structures as arteries, veins, and lymph nodes. Goldberg, B. B., et al., "Sonographically guided laparoscopy and mediastinoscopy using miniature catheter based transducers," *J Ultrasound Med* 12, 49–54 (1993); Liu, J. B., et al., "Transnasal US of the esophagus: preliminary morphologic and function studies," *Radiology*, 184, 721–727 (1992).

SUMMARY OF THE INVENTION

A brushed tipped catheter with incorporated ultrasound transducer is placed within the lumen of the tracheobronchial tree, preferably through a bronchoscope channel. Preferably, the catheter includes a plurality of bristles extending from a tapered distal end of the catheter and used as a biopsy brush. These bristles most preferably are all of substantially equal length extending radially for a distance of about 1 mm, and extend along an axial length of the sheath for about 8 mm. In preferred embodiments, the catheter has a diameter between 3.5–6.2 French, and most preferably has a diameter of 6.2 French.

The present invention also discloses methods for determining the location of a lesion in a subject's tracheobronchial tree by introducing a catheter-sheath containing an ultrasound transducer into the tracheobronchial tree and then activating the ultrasound transducer to produce an ultrasound image. The image is then reviewed to determine if a lesion exists, and if a lesion exists its position can then be determined. In accordance with the preferred embodiments of the present invention, the ultrasound images are analyzed to characterize the lesion, and a biopsy is performed on the lesion. Most preferably, the step of performing a biopsy comprises the step of manipulating a brush attached to the end of the catheter. The methods of the present invention can be used in conjunction with a fiberoptic bronchoscope and thus, in such embodiments, it will be preferred that the step of introducing the catheter comprises passing the catheter through biopsy port of the fiberoptic bronchoscope.

BRIEF DESCRIPTION OF THE DRAWINGS

FIG. 1 is a side elevation view of the distal end of an ultrasound catheter made in accordance with the present invention.

FIG. 2 is an end elevation of the ultrasound catheter shown in FIG. 1.

FIG. 3 illustrates a side elevation view similar to FIG. 1 illustrating an alternate embodiment of the present invention disposed within a dual lumen catheter.

FIG. 4 illustrates an end view of the dual lumen catheter embodiment shown in FIG. 3.

DETAILED DESCRIPTION OF THE PREFERRED EMBODIMENTS

Currently, peripheral transbronchial biopsies are performed blindly and rely on pre-examination review of previous films, computed tomography and magnetic resonance studies, and the use of fluoroscopy during the procedure for the biopsy of peripheral masses. The ultrasound bronchoscope of the present invention solves the problem of direct visualization of the lesion and the lung parenchyma surrounding the bronchus. Additionally, one is able to precisely biopsy the mass under direct ultrasound guidance. The advantage of this ability to simultaneously visualize the lesion and perform a brush biopsy should allow for a higher incidence of successful biopsies.

Referring now to FIG. 1, a brush tipped ultrasonic catheter assembly 100 comprising a catheter-sheath 110 having a lumen 112 and an ultrasound transducer-core 120 disposed within the catheter-sheath 110 is illustrated. The ultrasound transducer-core 120 is terminated at its distal end with an ultrasound transducer 122, which is rotated to provide visualization, as understood by those of skill in the art. In accordance with preferred embodiments of the present invention, a biopsy brush comprising a plurality of bristles 130 extending from a distal end of the catheter-sheath 110 is provided. As illustrated in FIGS. 1–2, the bristles 130 most preferably are all of substantially equal length and extend radially, for a distance of about 1 mm from the tapered distal end 114 of the catheter-sheath 110, and extend along the axial length of the catheter-sheath 110 for about 8 mm. In preferred embodiments, the ultrasound catheter-sheath 110 preferably has a diameter of 3.5–6.2 French, and most preferably, 6.2 French (2 mm). As explained in further detail below, the ultrasound transducer assembly catheter can be introduced into the patient via the biopsy port of a flexible bronchoscope, or via another method or mode of access, as will be understood by those of ordinary skill.

To improve the accuracy of peripheral lesion biopsy, the present invention thus provides an ultrasound transducer-containing catheter with a radial brush just distal to the ultrasound transducer fixed within the catheter sheath. With a brush-tipped ultrasound catheter made in accordance with the present invention, one is able to extend the field of interrogation of fiberoptic bronchoscopy with direct ultrasound imaging to the periphery of the lung. Although fluoroscopy may be used to help in guiding the radiopaque brush to the periphery of the lung, because it is not a three dimensional modality and it is possible, and in fact very frequent, that one is not able to biopsy the lesion in question. However, using the simultaneous imaging and brushing biopsy capability of the present invention, the percentage of successful biopsies is likely to increase dramatically. Since the brushing catheter is disposable and removable from the transducer, the initial cost of the transducer will be recaptured by the multiple uses of the transducer when placed within the relatively low priced catheters. This ability to reuse the transducer combined with disposable catheter brushes makes the disclosed device economically feasible.

Additionally, it will be realized that other "tools" can be affixed to the distal end of the sheath or disposed within the distal end of the sheath. As used herein the term "tool" is meant to broadly encompass any implement used within a patient, however, an inflatable device such as a PTCA (Percutaneous Transluminal Coronary Angioplasty) balloon is not considered to be a tool that canbe used with the present invention. Among such useful tools is a biopsy needle that would replace or supplant the brush-tipped assembly described above. Such a device is illustrated in FIG. 3. As shown, the needle 200 is encased in the end of the sheath, and as shown in phantom can be manipulated so it emerges at the appropriate biopsy site. As shown in FIGS. 3–4, the needle 200 is preferably carried in a second lumen 212 within a dual lumen catheter.

In addition to the use of the present invention as a bronchoscopic biopsy/imaging modality, it may also be used for other luminal indications in the gastrointestinal tract and the genitourinary tract, among others.

The following non-limiting Example illustrates the use of ultrasonic guided bronchoscopy as disclosed by the present invention to determine the site of a biopsy.

EXAMPLE I

To demonstrate the value of ultrasound guidance during flexible bronchoscopic procedures in a series of patients with known or suspected pulmonary neoplasms. ultrasound-guided bronchoscopy was carried out as an adjunct to conventional bronchoscopy for the diagnosis of mediastinal, hilar, or parenchymal neoplasms in 25 patients with masses previously detected with chest radiography or computed tomography. Miniature transducer-containing catheters were inserted through the biopsy port of a flexible bronchoscope, and cross-sectional real-time ultrasound scans of tumors, lymph nodes, and blood vessels were obtained. Among six cases of peripheral masses and 19 cases of central masses, additional information was provided in 18 cases (72%). This information was used to choose the optimal site for transmural biopsy. These results suggest that this ultrasound procedure is an important diagnostic tool during bronchoscopy, due to its ability to identify structures beyond the lumen of the tracheobronchial tree.

Materials and Methods

Ultrasound-guided bronchoscopy was performed for the diagnosis of central or peripheral lung masses (suspected at pre-procedural evaluation with computed tomography and/or plain radiography) as an adjunct to conventional fiberoptic bronchoscopy in 25 adults. Central lesions were defined as masses or lymph nodes in the mediastinum or hila to the level of second-order bronchi. Peripheral masses were defined as lesions surrounded by lung parenchyma subtended by or adjacent to third-order or more distal bronchi. The patients in this study included 18 women and seven men aged 43–83 years (mean, 63 years). The use of ultrasound during bronchoscopy was approved by the institutional review board, and informed consent was obtained from each patient. A 60-cm-long fiberoptic bronchoscope (Pentax Precision Instrument, Orangeburg, N.Y.) with an external diameter of 4.9 mm and a biopsy channel of 2.2 mm was used during the procedure. The biopsy port or working channel accepted a flexible 6.2 French 2 mm diameter, 95 cm-long catheter containing a single ultrasound transducer (Sonicath; Meditech/Boston Scientific, Watertown, Mass.) with a frequency of either 12.5 or 20 MHz attached to a ultrasound unit (IVUS; Diasonics, Milpitas, Calif.). The motor of the ultrasound unit continuously rotated the transducer 360° to produce a real-time cross-sectional image. The transducer was prepared by injecting 0.5–1.0 mL of sterile water between the transducer and the catheter to eliminate air, which could interfere with the transmission of the ultrasound beam.

In each case, the bronchoscope was inserted into the tracheobronchial tree and passed to the area of interest as determined by previously obtained chest radiographs and/or computed tomography scans. The computed tomography examinations were performed with a third-generation scanner (9800 Quick; GE Medical Systems, Milwaukee, Wis.) with or without contrast enhancement, with use of 10-mm sections through the chest and 5-mm sections through the hila.

The fiberoptic lens located at the distal end of the bronchoscope permitted visualization of the mucosal surface. Mural distortion of the bronchial surface by an extraluminal mass and/or luminal obstruction, if present, was documented. Fluoroscopy was used to localize the tip of the bronchoscope and the biopsy instrument relative to the dominant mass.

The miniature transducer-containing catheter was then inserted by the bronchoscopist through the biopsy port. The tip for the ultrasound catheter could be easily seen on the video monitor as it exited the port adjacent to the end of the bronchoscope. The side of the distal end of the ultrasound catheter containing the rotating transducer was placed against the tracheobronchial mucosa in the region of the suspected abnormality. Bronchial secretions were usually sufficient to create acoustic coupling, allowing the ultrasound beam to penetrate into adjacent tissues, producing a cross-sectional image at about 2 cm of depth with an axial resolution of 0.1 mm. The images were available for interpretation in real time to guide the radiologist and bronchoscopist to the site of the abnormality. The real-time images were recorded on videotape for later evaluation, and individual frozen frame images were stored on a digital imaging disk system (3M Medical Imaging System, St. Paul, Minn.).

To evaluate masses in the periphery of the lung, the ultrasound catheter was advanced beyond the distal end of the bronchoscope. It was usually possible to obtain a 360° image at the level of the fourth- to sixth-order bronchi, unlike at the level of the larger bronchi and the trachea, where only a wedge of ultrasound information was obtained because the transducer could be maintained in contact with only a portion of the wall.

The exact site for biopsy was determined and compared with the previously selected site with use of the standard bronchoscopic method before insertion of the ultrasound transducer. After selection of a biopsy site, the ultrasound catheter was removed and the biopsy instrument was inserted through the same port in the bronchoscope. The bronchoscopist then positioned the biopsy catheter at the abnormality site selected with ultrasound, aided by a C-arm portable fluoroscopic unit (Siemens, Erlangen, Germany). For peripheral lesions, this involved passing the biopsy instrument into the same bronchial lumen previously localized with the ultrasound transducer. For central lesions, endobronchial landmarks identified with ultrasound served as a guide to selection of an appropriate site for biopsy.

The diagnostic usefulness of the ultrasound information was evaluated by both the radiologist and bronchoscopist on a scale of 0 to 3. Category 0 meant that ultrasound was technically inadequate and did not contribute to the performance of the examination. Category 1 meant that disease and anatomy were demonstrated, but this did not aid in localization for transbronchial biopsy. Category 2 meant that use of ultrasound guidance was helpful in the separation of vessels from lymph nodes or masses but did not alter the site of biopsy. Category 3 meant that ultrasound was useful in altering the biopsy site to a location in which the abnormality was seen to better advantage (category 3a) and/or was helpful in preventing invasion of a blood vessel (category 3b).

Results

In the 25 patients examined, there were six peripheral and 19 central masses. In 12 cases (48%), ultrasound guidance was very helpful because its use altered the choice of the biopsy site (category 3a). In this group of 12 cases, ultrasound information helped to avoid biopsy of a blood vessel (category 3b) in eight cases. Ultrasound guidance was helpful in identifying the specific site for biopsy of lymph nodes or masses in six cases (24%) (category 2). Overall, additional information was provided in 18 of the 25 cases (72%). In an additional five cases (20%), anatomic information was provided that did not aid in tumor localization for transbronchial biopsy (category 1). It was only in two patients (8%) that ultrasound was technically inadequate (category 0). These were cases in which it was difficult to maintain adequate contact with the wall of the bronchus in order to obtain useful information. Ultrasound added approximately five minutes to the length of the bronchoscopic procedure. However, the information elicited with ultrasound may have actually shortened the procedure in some cases by eliminating the need for additional biopsies owing to appropriate initial localization of the area of interest.

The masses localized in this Example were usually of decreased echogenicity compared with that of the surrounding tissue, but, in a few cases, the echotexture was complex, exhibiting both hyper- and hypoechogenic reflections (thought to represent areas of necrosis) and/or hemorrhage within the mass. Peripheral masses often had sharply defined borders due to the strong deflective interfaces produced between the aerated lung and the lesion. Adjacent zones of atelectasis tended to be more reflective than the tumor itself, probably due to the multiple interfaces produced by the airless lung parenchyma mixed with alveolar secretions and residual air-filled acini.

In addition to simply identifying the mass in question, dimensions of the lesion could also be delineated up to 2 cm from the bronchial wall with ultrasound. This limitation was not considered serious because the dimensions of the tumor were usually appreciated from inspection of the previously obtained chest radiograph or computed tomography scan. More important, the location of the tumor in relation to the bronchus in which the transducer was located could be determined. In some cases, tumors were found to be eccentric, with their surface abutting only on a small portion of the bronchus, whereas in others the masses were seen to completely surround the bronchus. Although the tracheal and bronchial walls were normally hyperechogenic, when the tumor invaded the bronchial wall this pattern disappeared and the bronchial wall tended to blend in with the adjacent hypoechogenic tumor.

As the transducer moved along the surface of the bronchus or trachea, the extent of the tumor and its maximum depth could be demonstrated. This was most dramatically seen in cases of peripheral tumors, in which the relatively small bronchus usually permitted complete contact with the transducer-containing catheter, resulting in a 360° cross-sectional ultrasound image. These peripheral tumors were usually beyond the reach of the bronchoscope, and thus additional information not previously available with standard bronchoscopy was provided by these small-diameter transducers. In cases of peripheral masses, transbronchial biopsy was successful in five of six patients. No adjacent blood vessels were demonstrated that would be of concern during the biopsy procedure, and, as expected, no peripherally located lymph nodes were imaged.

Lymph nodes were characterized as discrete, well-marginated, hypoechogenic structures, usually ovoid or, in some cases, round. A hyperechogenic center was sometimes demonstrated and was thought to be produced by the reflective fatty hilus of the lymph node. This typical pattern of normal lymph nodes has been demonstrated in other regions of the body. See Vasallo et al., "Differentiation of benign from malignant superficial lymphadenopathy: the role of high-resolution US," *Radiology*, 183, 215–220 (1992). With ultrasound, the distance of lymph nodes from the tracheal or bronchial wall could be measured. In cases of central lesions, both the tumor and lymph nodes were successfully sampled under ultrasound guidance in 15 of 19 cases.

Blood vessels were demonstrated as anechoic tubular or oval structures. In several cases, actual vessel branching could be imaged. Arteries demonstrated pulsatility. However, veins were free of pulsations, unless transmitted from adjacent vascular or cardiac structures. They usually contained slowly moving echoes due to reflections related to red blood cell roleau formation. The diameter of the blood vessels could be measured and their position relative to the bronchus, tumor, or lymph nodes could be demonstrated. With this information, it was possible to avoid puncturing blood vessels by choosing a site for transbronchial biopsy away from these vital structures. In six patients, inadvertent biopsy of blood vessels was thus avoided.

From within the main bronchus or trachea, it was sometimes possible to visualize a portion of the cardiac structures. While no masses were demonstrated in paracardiac zones in this series, inadvertent pericardial or cardiac biopsy under ultrasound guidance will be avoided when a mass occurs adjacent to these cardiac structures.

Endoluminal ultrasound has an advantage over fluoroscopy in locating the lesion in relationship to the bronchus into which the biopsy forceps or needle is placed. Unlike fluoroscopy, ultrasound can show whether the lesion lies beyond the mucosa or demonstrates mucosal invasion. It can also enable evaluation of the depth of the mass and the presence or absence of lymph nodes adjacent to the bronchial wall. In addition, ultrasound catheters allow distinction of blood vessels from nonvascular masses. This may reduce the incidence of hemorrhage, although significant hemorrhage has not been a frequent problem in transbronchial biopsy performed with use of conventional fluoroscopically guided biopsy techniques.

In the trachea and major bronchi, it was not possible to obtain a 360° cross-sectional image because the lumen diameters were much larger than the transducer-containing catheters. Thus, only that portion of the transducer that was in contact with the mucosal surface yielded a ultrasound image. Since the tracheal cartilaginous rings were often too thick to allow penetration of the ultrasound beam, it was necessary to position the transducer in the space between those rings. This did not present a serious problem, since it was also necessary to avoid the cartilaginous rings when the site for biopsy was selected. The bronchoscopist was able in most cases to obtain a series of ultrasound images at various levels, permitting localization of the primary mass and/or lymph nodes in all but two cases. Attempts were made to precisely localize the site at which to apply the transducer to the mucosal surface by reviewing the previously obtained chest radiographs or computed tomography scans and/or by observing bronchoscopically any distortion of the surface of the trachea or bronchus. As with peripheral lesions, tumors tended to be hypoechogenic and were either homogeneous or heterogeneous, depending on the presence of fibrosis, mucus secretions, calcification, hemorrhage, and/or necrosis.

The limitations of the procedure may be avoided by improvements in both the ultrasound catheter and bronchoscopic technology. For example, the addition to the transducer-containing catheter of an inflatable balloon that could be dilated so as to maintain contact of the transducer to the wall of the trachea and the larger bronchi would be helpful. Similar inflatable balloon-tipped ultrasound transducers incorporated into endoscopes for evaluation of the esophagus are currently in use. See Rifkin et al., "Sonographic examination of the mediastinum and upper abdomen by fiberoptic gastroscope," *Radiology*, 151, 175–180 (1984). Bronchoscopes in accordance with the present invention will preferably have built-in ultrasound transducers, however, this would not solve the problem of evaluating peripheral tumors, for which a separate ultrasound catheter would be preferable. To improve the accuracy of tumor biopsy, bronchoscopes that have dual working channels can be used, with the ultrasound catheter advanced through one opening and the biopsy catheter through the other. If this is done, a biopsy can be performed at the same time as ultrasound. With this approach, it is possible to record reflections from the biopsy needle as it moves toward and then into the tumor and/or lymph node for biopsy. This would allow confirmation of the exact site of the biopsy and reduce the need for fluoroscopy, which is now used to confirm the position of the transducer and biopsy catheter in peripheral masses.

Thus, ultrasound has been shown to be an important adjunct to bronchoscopy owing to its capability to locate structures beyond the lumen of the tracheobronchial tree as well as to localize peripheral masses distal to the current range of conventional fiberoptic bronchoscopic catheters.

Information related to this Example is found in Steiner et al., "Ultrasound-Guided Fiberoptic Bronchoscopy of Peripheral Pulmonary Masses Using Catheter-Based Miniature Transducers", 79th Scientific Assembly and Annual Meeting of Radiologic Clinics of North America, Nov. 28–Dec. 3, 1993, McCormick Place, Chicago, Ill.; and Liu et al., "Bronchoscopic Ultrasound" 79th Scientific Assembly and Annual Meeting of Radiologic Clinics of North America, Nov. 28–Dec. 3, 1993, McCormick Place, Chicago, Ill. Both of which are incorporated herein by reference.

Although certain embodiments of the methods and apparatus of the present invention have been set forth above in great detail, these examples are meant to illustrate the invention and do not limit its scope. Numerous variations, adaptations and modifications will present themselves to those of skill in the art upon review of the foregoing specification. Accordingly, reference should be made to the appended claims in order to determine the full scope of the present invention.

What is claimed is:

1. An ultrasonic catheter assembly comprising a catheter sheath and an ultrasound transducer disposed within the catheter sheath, wherein a non-inflatable tool is affixed to and extends radially beyond an exterior surface of the catheter sheath near a distal end of the catheter sheath at a point proximal of the distal end.

2. The ultrasonic catheter assembly of claim 1 wherein the tool comprises a plurality of bristles extending radially from a distal end of the catheter sheath.

3. The ultrasonic catheter assembly of claim 2 wherein the bristles extend radially for a distance of about 1 mm.

4. The ultrasonic catheter assembly of claim 2, wherein the bristles extend along an axial length of the catheter sheath for about 8 mm.

5. The ultrasonic catheter assembly of claim 2 wherein the distal end of the catheter sheath is tapered.

6. The ultrasonic catheter assembly of claim 2, wherein the bristles are all of substantially equal length.

7. The ultrasonic catheter assembly of claim 1, wherein the catheter has a diameter between 3.5–6.2 French.

8. A method of determining the location of a lesion in a subject's tracheobronchial tree and obtaining sample tissue from the lesion in a single procedure comprising the steps of:

introducing a catheter sheath containing an ultrasound transducer into the tracheobronchial tree;

activating the ultrasound transducer to produce an ultrasound image;

reviewing the ultrasound image to determine if a lesion exists;

determining the position of the lesion;

extending a biopsy tool for obtaining a tissue sample from within the sheath; and performing a biopsy while simultaneously imaging the lesion.

9. The method of claim 8, further comprising the step of analyzing the ultrasound image to characterize the lesion.

10. The method of claim 8, wherein the step of performing a biopsy comprises the step of manipulating a brush attached to the end of the catheter.

11. The method of claim 8, wherein the step of introducing the catheter comprises passing the catheter through biopsy port of a fiberoptic bronchoscope.

12. The method of claim 8, wherein the step of performing a biopsy comprises inserting a biopsy needle into the catheter sheath.

* * * * *